United States Patent [19]

Yamashita

[11] Patent Number: 5,556,768

[45] Date of Patent: Sep. 17, 1996

[54] METHOD FOR PREPARING PEPTIDES AND PROTEINS UTILIZING RIBOSOME

[75] Inventor: Nobuhiko Yamashita, Takatsuki, Japan

[73] Assignee: Osaka Gas Company Limited, Osaka, Japan

[21] Appl. No.: 266,750

[22] Filed: Jun. 28, 1994

[30] Foreign Application Priority Data

Jun. 29, 1993 [JP] Japan .................................. 5-158662

[51] Int. Cl.$^6$ ...................................................... C12P 21/02
[52] U.S. Cl. ......................... 435/69.1; 435/68.1; 935/44; 935/45
[58] Field of Search ................................. 435/68.1, 69.1; 935/44, 45

[56] References Cited

PUBLICATIONS

McKay, F. C., et al, J. Am. Chem. Soc., 79, 4686–4690 (1957).
Carpino, L. A., et al, J. Am. Chem. Soc., 92, 5748–5749 (1970).
Merrifield, R. B., J. Am. Chem. Soc., 85, 2149–2154 (1963).
Bergmann, M., et al, J. Biol. Chem., 124, 1–6 (1938).
Hedgpeth, J., et al, Proc. Nat. Acad. Sci. USA, 69, No. 11, 3448–3452 (1972).
Nirenberg, M. W., et al, Proc. Nat. Acad. Sci. USA, 47, 1588–1602 (1961).
Oka, T., et al, J. Biochem. 84, 1277–1283 (1978).
Takai, H., et al, Peptide Chemistry 1980, K. Okawa, ed., Protein Research Foundation, 213–218 (1981).
Nakajima, H., et al, Biochimica et Biophysica Acta 790, 197–199 (1984).
Spirin, A. S., et al, Science, 242, 1162–1164 (1988).
Heckler, T. G., et al, Tetrahedron, 40, 87–94 (1984).
Heckler, T. G., Biochemistry, 23, 1468–1473 (1984).
Heckler, T. G., et al, J. Biol., Chem., 258, 4492–4495 (1983).
Roesser, J. R., et al, Biochemistry, 25, 6361–6365 (1986).
Payne, R. C., et al, Biochemistry, 26, 3197–3205 (1987).
Noren, C. J., et al, Science, 244, 182–188 (1989).
Noll, M., et al, J. Mol. Biol., 75, 281–294 (1973).
Usman, N., et al, J. Amer. Chem. Soc., 109, 7845–7854 (1987).
Ogilvie, K. K., et al, Proc. Natl. Acad. Sci. USA, 5764–5768 (Aug. 1988).
Spedding, G., "Ribosomes and Protein Synthesis," G. Spedding, ed., Oxford University Press, pp. 22–27 (1989).

*Primary Examiner*—Charles L. Patterson, Jr.

[57] ABSTRACT

A novel method for synthesizing peptides and proteins having a desired amino acid sequence by utilizing an aminoacyl-tRNA and misaminoacyl-tRNA as well as an artificial mRNA in a system for in vitro protein synthesis is provided. According to the present method, desired peptides and proteins can be synthesized using naturally-occurring and non naturally-occurring amino acids. Accordingly, the present invention provides a fundamental technique which is important in the fields of various industries and various fundamental researches such as biochemistry, molecular biology and protein engineering.

7 Claims, 7 Drawing Sheets

Analysis of Phe-Glu-Phe synthesized by step reaction in a system for in vitro protein synthesis via reverse phase chromatography

Fig. 7

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 15 bases
( B ) TYPE: nucleic acid (C) STRANDEDNESS: single
(D) TOPOLOGY: linear (ii) MOLECULE TYPE: mRNA (xi) SEQUENCE DESCRIPTION: SEQ ID NO:1:

AUGUUUGAGU UUGAG   15

(2) INFORMATION FOR SEQ ID NO:2:

(i) SEQUENCE CHARACTERISTICS:
    (A) LENGTH: 12 bases
    (B) TYPE: nucleic acid
    (C) STRANDEDNESS: single
    (D) TOPOLOGY: linear (ii) MOLECULE TYPE: mRNA (xi) SEQUENCE DESCRIPTION: SEQ ID NO:2:

UUUGAGUUUG AG   12

(2) INFORMATION FOR SEQ ID NO:3:

(i) SEQUENCE CHARACTERISTICS:
    (A) LENGTH: 4 amino acids
    (B) TYPE: amino acid
    (D) TOPOLOGY: linear (ii) MOLECULE TYPE: peptide (xi) SEQUENCE DESCRIPTION: SEQ ID NO:3:

Phe  Glu  Phe  Glu
1

(2) INFORMATION FOR SEQ ID NO:4:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (xi) SEQUENCE DESCRIPTION: SEQ ID NO:4:

Met  Phe  Glu  Phe  Glu
1                    5

METHOD FOR PREPARING PEPTIDES AND PROTEINS UTILIZING RIBOSOME

FIELD OF THE INVENTION

The present invention relates to a novel method for preparing peptides and proteins. In particular, it relates to a method for synthesizing peptides and proteins having a desired amino acid sequence by utilizing an aminoacyl-tRNA and misaminoacyl-tRNA as well as an artificial mRNA.

PRIOR ART

Peptides and proteins are widely utilized in various industrial fields such as medicine, food, chemical, and electronic industries. On the other hand, a technique for molecular design of a protein utilizing a computer has developed in recent years, and interests are directed to research on correlations between structure and function of a protein and to development of protein engineering based on findings obtained by the research. In order to satisfactorily realize the fruits of the protein engineering, it is necessary to synthesize a protein having various amino acid sequence in a short time.

At present, there exist several methods for synthesizing peptides and proteins such as chemical, enzymatic and recombinant methods, and a method utilizing a system for in vitro protein synthesis.

The chemical method for synthesizing a peptide is that wherein the peptide is synthesized stepwise using amino acids constituting the peptide (wherein amino group and functional groups of side chains of the amino acids are suitably protected) and a condensing agent. As a protecting group of the amino group, t-butyloxycarbonyl group (t-Boc group)(reference 1; all the references cited herein are listed below) or 9-fluorenylmethyloxycarbonyl group (F-moc group)(reference 2) may be mentioned. As a condensing agent, dicyclohexylcarbodiimide (DCC) is frequently used. The reaction is carried out by liquid phase or solid phase technique.

In the liquid phase technique, reaction is carried out in a solution in a similar manner as a conventional organic synthesis. Since a synthetic cycle consisting of reaction and purification is required for addition of every amino acid, this technique needs much time and labor. However, the technique gives a highly purified peptide.

In the solid phase technique, a peptide is prepared on a carrier. That is, a C-terminal amino acid of a desired peptide is immobilized on an insoluble carrier such as polystyrene or polyacrylamide and the peptide is extended on the carrier. The technique was developed in 1963 by Merrifield (reference 4). Although the technique does not allow purification during preparation process, it is easy to manipulate, it is possible to automate, and an automated synthesizer is publicly marketed. The automated synthesizer can be used to synthesize a peptide having about 40 amino acid residues.

However, both techniques have a defect that separation of side products produced in a trace amount besides the desired product is very difficult. Furthermore, since the side products accumulate exponentially by repeating the condensation reaction, it is not possible to synthesize a protein having a large 10 molecular weight. However, the chemical methods have an advantage that they permit to synthesize a peptide containing a non-naturally occurring amino acid.

The enzymatic method utilizes an enzyme in condensation reaction of amino acids and two methods are known in the art: reverse synthesis of peptide bonds utilizing a protease and synthesis utilizing aminoacyl-tRNA synthetase (ARS).

The first case of peptide synthesis utilizing a protease was reported by Bergmann et al. in 1938 (reference 5), wherein a protected dipeptide was reverse-synthesized using papain. In addition to papain, proteases such as α-chymotrypsin, carboxypeptidase Y, trypsin, and pepsin were used as an enzyme (reference 6), and many types of peptides have been prepared (reference 7).

On the other hand, the method utilizing ARS uses as a nucleophilic component an aminoacyl-AMP-ARS complex which is an intermediate of aminoacylation reaction of tRNA, and a peptide is formed by stepwise reaction of a second amino acid component (reference 8).

Synthesis of a peptide by the enzymatic methods shows a poor condensation efficiency. Accordingly, these methods are used only for synthesizing a small peptide or chimera protein and not suitable for whole synthesis of a protein by stepwise reaction.

The recombinant method is that wherein a desired protein is synthesized in vivo by incorporating a gene of the desired protein into a suitable host-vector system and producing the desired protein in the host organism. According to the method, it is possible to synthesize a protein having a large molecular weight which can not be synthesized by the above chemical or enzymatic method. However, for expressing a desired gene in a microorganism at a practical level by the method, it is necessary to conquer many difficulties, such as selection of an expression vector suitable for the desired gene, establishment of culturing conditions of the microorganism, separation and purification of expression products. Furthermore, production of a toxic protein or a small peptide susceptible to an attack of endogenous proteolytic enzymes is accompanied by a great difficulty. In addition, binding of an amino acid to tRNA is strictly controlled by aminoacyl-tRNA synthetase in the case of in vivo synthesis, and therefore, it is almost impossible to introduce a non-naturally-occurring amino acid into a protein.

The synthetic method utilizing a system for in vitro protein synthesis is a method for synthesizing a desired protein by transferring a system for intracellular protein synthesis derived from *E. coli* and the like to a test tube and adding to the system a gene or mRNA for the desired protein and various factors necessary for the protein synthesis. A system for in vitro protein synthesis depending on an exogenous mRNA was first established by Nirenberg et al. in 1961 (reference 10), and thereafter, many systems for in vitro protein synthesis have been prepared using many organisms. Since, however, the reaction generally stops within several hours in a batch synthesis, it is difficult to obtain a practical level of protein. Recently, Spirin et al. developed a system providing mg scale of a desired protein by successively supplying necessary substrates to the system to extend the reaction time up to several ten hours (reference 11). The method have, for example, the following advantages: purification procedures of the desired protein from a host organism can be largely simplified; a toxic protein or a peptide susceptible to decomposition by proteolytic enzymes can be synthesized; and a protein containing a non-naturally-occurring amino acid can be synthesized.

As described above, a synthetic method by a recombinant technique and a system for in vitro protein synthesis allow preparation of a high molecular weight of protein which is impossible to be prepared by chemical and enzymatic methods. In addition, the synthetic method by a system for in vitro protein synthesis allows preparation of a protein containing a non-naturally-occurring amino acid. In synthesizing a desired protein by utilizing a recombinant technique and a system for in vitro protein synthesis, however, information for an amino acid sequence of the desired protein must be previously prepared in the form of DNA or mRNA. Thus, these genes must be previously cloned from other organisms or synthesized by a chemical means. Accordingly, when the primary structure of a particular protein is to be partially modified or a peptide or protein having a particular amino acid sequence is to be synthesized, it is necessary to add steps wherein the required gene is prepared and modified. These steps include complex experimental procedures utilizing an *E. coli* host-vector system such as cloning of the desired gene from an organism or chemical synthesis of the gene, purification, sequencing and partial modification of the gene. Accordingly, when a protein having a totally novel amino acid sequence is to be synthesized and when the primary structure of such protein is to be drastically modified, the synthetic method by a recombinant technique or a system for in vitro protein synthesis is not sufficient.

As described above, the synthetic method utilizing a system for in vitro protein synthesis is suitable for synthesizing various naturally-occurring peptides or proteins as well as non-naturally-occurring amino acid-containing peptides or proteins. In this method, however, information for an amino acid sequence exists on mRNA, and therefore, it is difficult to rapidly prepare a desired protein by voluntarily modifying the primary structure of a protein or to introduce multiple non-naturally-occurring amino acids into the protein.

Thus, the present inventor has intended to obtain a method for synthesizing a peptide or protein having a desired amino acid sequence in a system for in vitro protein synthesis, without defining the order of the amino acid sequence of the desired peptide or protein by endogenous mRNA but defining it by instructions from the outside of the system.

In synthesizing a protein in vivo or in vitro, a genetic code on mRNA is translated to a protein in ribosome. Triple base chain (genetic codon) of mRNA is a unit of the genetic code and there exist 64 types of codons. An aminoacyl-tRNA reads the genetic code on mRNA as information for an amino acid sequence, and specific tRNAs exist for each of 61 types of genetic codons other than stop codons. To each tRNA is bound a defined amino acid by aminoacyl-tRNA synthetase (ARS). A strict specificity of ARS assures exact correspondence of an amino acid to a genetic codon.

Recently, Hecker et al. showed that a misaminoacyl-tRNA (wherein a natural amino acid does not bind to tRNA but other amino acid or non-naturally-occurring amino acid binds to the tRNA) can be chemically synthesized (references 12 and 13). It has been shown that such a misaminoacyl-tRNA serves as a substrate in a system for protein synthesis utilizing ribosome in a similar manner as a normal aminoacyl-tRNA and an amino acid bound to the misaminoacyl-tRNA is incorporated into a protein (references 14, 15 and 16).

Furthermore, Shultz et al. successfully incorporated a non-naturally-occurring amino acid site-specifically into β-lactamase protein in a system for in vitro protein synthesis, by chemically binding various non-naturally-occurring amino acids to suppressor-tRNA recognizing UAG codon (stop codon) to synthesize an artificial misaminoacyl-tRNA and by substituting UAG codon for a specific site of β-lactamase gene (reference 17).

Thus, it is possible to incorporate a desired amino acid or non-naturally-occurring amino acid into a protein by artificially changing a linkage of tRNA and an amino acid to synthesize a misaminoacyl-tRNA.

The present inventor considered that it might be possible to synthesize a peptide or protein having a desired amino acid sequence by carrying out a stepwise extension reaction in a system for in vitro protein synthesis using an artificial mRNA having a predetermined sequence and the above misaminoacyl-tRNA, and carried out an intensive research. As a result, the present invention has been accomplished.

BRIEF DESCRIPTION OF THE INVENTION

Thus, the present invention provides a novel method for synthesizing a peptide or protein having a desired amino acid sequence by a stepwise extension reaction comprising:

(i) preparing as a template an artificial mRNA having a repeat structure of multiple genetic codons different from each other;

(ii) preparing an aminoacyl-tRNA (wherein a corresponding naturally-occurring amino acid binds to tRNA) and misaminoacyl-tRNAs (wherein a non-corresponding naturally-occurring or non-naturally-occurring amino acid binds to tRNA), said aminoacyl-tRNA and misaminoacyl-tRNAs each corresponding to each of said multiple genetic codons; and (iii) adding only aminoacyl-tRNAs or misaminoacyl-tRNAs (wherein an amino acid component to be incorporated into said peptide or protein binds to tRNA) to a system for in vitro protein synthesis containing said mRNA and ribosome, and extending stepwise the chain of said peptide or protein.

According to the present method, it is possible to synthesize a desired peptide or protein utilizing a naturally-occurring amino acid and non-naturally-occurring amino acid. Thus, the present invention provides a fundamental technique which is important in the fields of various industries and various fundamental researches such as biochemistry, molecular biology and protein engineering.

DETAILED DESCRIPTION OF THE INVENTION

The simplest example in practicing the present invention is the case wherein the number of multiple 10 genetic codons which are different from each other is two. In this case, an artificial mRNA wherein these two genetic codons are arranged alternately is used as a template.

On the other hand, for each of two tRNAs corresponding to the above two genetic codons, an aminoacyl-tRNA (wherein a corresponding naturally-occurring amino acid binds to tRNA) and misaminoacyl-tRNAs (wherein a non-corresponding naturally-occurring or non-naturally-occurring amino acid binds to tRNA) are prepared.

Then, a peptide having a desired amino acid sequence can be synthesized by adding only an aminoacyl-tRNA or misaminoacyl-tRNA (wherein an amino acid component to be incorporated into the peptide binds to tRNA) to a system for in vitro protein synthesis containing the above mRNA and ribosome, and carrying out stepwise extension reaction of the peptide chain.

For example, synthesis of tripeptide, alanyl-glycyl-tyrosine, by step reaction is described below. As an artificial mRNA, for example, mRNA comprising a repeat structure of a base sequence UUUGAG is prepared utilizing genetic codons UUU and GAG coding for phenylalanine and glutamic acid, respectively.

The artificial mRNA and S-100 fraction as well as a suitable buffer containing components necessary for in vitro protein synthesis are added to ribosome prepared from $E.\ coli$. Then, to the mixture is added a misaminoacyl-tRNA wherein the first amino acid of the desired peptide, alanine, binds to tRNA$^{Phe}$ (corresponding amino acid is phenylalanine, and the tRNA forms a complex together with a codon for phenylalanine on mRNA), and the mixture is reacted at about 37° C. for an appropriate time (for example, 15 minutes). By the reaction, a bond is formed between the phenylalanine codon on mRNA, ribosome and alanyl-tRNA$^{Phe}$ to give a complex. At this time, the next codon of the phenylalanine codon on mRNA is a codon for glutamic acid and there exists no aminoacyl-tRNA$^{Glu}$ in the reaction system, and therefore, the peptide-forming reaction can not proceed ahead.

The complex is separated from other components, for example, by a means such as molecular sieve chromatography. The complex fraction is then concentrated, for example, by a means such as ultrafiltration. The ribosome-mRNA-alanyl tRNA$^{Phe}$ complex thus concentrated can be used for binding the second amino acid of the desired peptide.

Thus, to the concentrated complex fraction are added S-100 fraction, a suitable buffer containing components necessary for in vitro protein synthesis, and glycyl-tRNA$^{Glu}$ wherein the second amino acid of the desired peptide, glycine, binds to tRNA$^{Glu}$, and the mixture is again reacted at about 37° C. for an appropriate time. As a result, a reaction between the first misaminoacyl-tRNA (alanyl-tRNA$^{Phe}$) and the second misaminoacyl-tRNA (glycyl-tRNA$^{Glu}$) on ribosome takes place to give alanyl-glycyl-tRNA$^{Glu}$. At this time, alanyl-glycyl-tRNA$^{Glu}$ binds to the glutamic acid codon on mRNA and the next codon is a codon for phenylalanine. However, there exists no aminoacyl-tRNA$^{Phe}$ in the reaction system, and therefore, the peptide-forming reaction can not proceed ahead. Accordingly, only alanyl-glycine is formed.

Then, the ribosome-mRNA-alanyl-glycyl-tRNA$^{Glu}$ complex is again separated from other components by molecular sieve chromatography, and the complex fraction is concentrated by ultrafiltration.

To the resulting complex fraction are added S-100 fraction, a suitable buffer containing components necessary for in vitro protein synthesis, and tyrosyl-tRNA$^{Phe}$ wherein the third amino acid of the desired peptide, tyrosine, binds to tRNA$^{Phe}$, and the mixture is again reacted at about 37° C. for an appropriate time. As a result, a reaction between the alanyl-glysyl-tRNA$^{Glu}$ and the tyrosyl-tRNA$^{Phe}$ on ribosome takes place to give alanyl-glycyl-tyrosyl-tRNA$^{Phe}$. At this time, alanyl-glycyl-tyrosyl-tRNA$^{Phe}$ binds to the phenylalanine codon on mRNA and the next codon is a codon for glutamic acid. However, there exists no aminoacyl-tRNA$^{Glu}$ in the reaction system, and therefore, the peptide-forming reaction can not proceed ahead. Accordingly, only alanyl-glycyl-tyrosine is formed.

After the desired peptide is thus synthesized, an RNA fraction containing the peptidyl-tRNA can be obtained from the reaction mixture, for example, by phenol extraction. The desired peptide can be eliminated from tRNA by decomposing RNA, for example, by alkaline hydrolysis of the RNA fraction. Then, the mixture of the desired peptide obtained and the decomposed products of RNA can be applied to a purification procedure such as reverse phase chromatography to obtain only the desired peptide.

Thus, the above-mentioned reaction for stepwise synthesis of a peptide can be divided into three reaction cycles: (a) Initiation reaction cycle wherein an aminoacyl-tRNA or misaminoacyl-tRNA (wherein a N-terminal amino acid of the desired peptide or protein binds to tRNA) forms a complex together with ribosome and mRNA; (b) Peptide extension reaction cycle wherein a peptide chain is extended stepwise from the second amino acid residue of the desired peptide or protein on the ribosome-mRNA-(mis)aminoacyl tRNA complex; and (c) Termination reaction cycle wherein the desired peptide or protein is separated from the ribosome-mRNA-peptidyl tRNA complex.

Initiation reaction cycle (a) is composed of the following three steps: (a-1) reaction of an aminoacyl-tRNA or misaminoacyl-tRNA (wherein a N-terminal amino acid of the desired peptide or protein binds to tRNA) with ribosome and mRNA to form a ribosome-mRNA-(mis)aminoacyl tRNA complex; (a-2) separation of the ribosome-mRNA-(mis) aminoacyl tRNA complex by high-performance molecular sieve chromatography; and (a-3) concentration of fractions containing the complex by ultrafiltration.

Peptide extension reaction cycle (b) is reaction cycles for binding amino acids stepwise one by one, and composed of the following three steps: (b-1) peptide formation reaction comprising binding the (N+1)th amino acid residue on the ribosome-mRNA-peptidyl tRNA complex (wherein the peptidyl contains N amino acids, and N is an integer of 1 or more); (b-2) separation of the resulting ribosome-mRNA-peptidyl tRNA complex by high-performance molecular sieve chromatography; and (b-3) concentration of fractions containing the complex by ultrafiltration. By repeating the reaction cycle, a desired number of amino acids can bind stepwise and a peptide having a desired amino acid sequence can be synthesized.

Termination reaction cycle (c) is composed of the following three steps: (c-1) recovery of the peptidyl-tRNA from the final ribosome-mRNA-peptidyl tRNA complex by phenol extraction and ethanol precipitation; (c-2) elimination of the desired peptide or protein from the peptidyl-tRNA by hydrolysis of RNA; and (c-3) purification of the desired peptide or protein by high-performance reverse phase chromatography.

In the above description, exemplified is the case wherein the number of multiple genetic codons different from each other is two, that is, the case wherein an artificial mRNA wherein these two genetic codons are arranged alternately is used as a template. However, it is also possible to use more genetic codons different from each other. Thus, the artificial mRNA used in the present method may comprise the following sequence:

$$(A_1 A_2 A_3 \ldots A_m)_n$$

wherein m is an integer of 2 to 64, n is an integer of 1 or more, m×n is equal to the number of amino acid residues of a desired peptide or more, and each of $A_1, A_2, A_3, \ldots$ and $A_m$ represents a genetic codon which differs from the other codons.

For example, when an artificial mRNA having a repeat structure of five codons different from each other is used as a template, it is possible to use four aminoacyl-tRNAs or misaminoacyl-tRNAs per one cycle of Peptide forming reaction cycle (b), and therefore, it is possible to extend four amino acids per one cycle at one time. Since tRNA can discriminatingly recognize at least twenty codons, it is possible to bind nineteen amino acids per one cycle at one time by using as a template an artificial mRNA having a repeat structure composed of twenty codons different from each other. Thus, according to the present method, it is possible to synthesize a long peptide in a small cycle number, and therefore, it becomes possible to synthesize a protein which has previously been difficult to prepare by chemical synthesis.

Materials and methods

In general, *E. coli*-derived ribosome and S-100 fraction (containing various factors for protein synthesis which are necessary for a system for in vitro protein synthesis) used in practicing the present invention can be prepared according to the method of Noll et al.(reference 18). Thus, *E. coli* (for example, MRE600) at mid log growth phase is ground together with aluminum oxide in a buffer solution containing 10 mM magnesium ion (for example, 20 mM Tris-HCl, 10 mM $(CH_3COO)_2Mg$, 100 mM $NH_4Cl$, 3 mM 2-mercaptoethanol (pH 7.5)), and DNase I was further added to decompose endogenous DNA. The sample solution is then centrifuged (for example, at 30,000 ×g for 45 minutes) to obtain a supernatant (S-30 fraction). The S-30 fraction is overlayered on equal volume of buffer solution B (for example, 10 mM Tris-HCl (pH 7.5) containing 1.1M sucrose, 10 mM $(CH_3COO)_2Mg$, 60 mM $NH_4Cl$, and 3 mM 2-mercaptoethanol), and it is centrifuged using ultracentrifuge for separation such as BECKMAN MODEL L8M (for example, at 100,000×g for 20 hours). Ribosome is recovered as a clear precipitation. On the other hand, the supernatant contains various factors necessary for protein synthesis, and can be used as S-100 fraction in a system for in vitro protein synthesis.

As mRNA having a repeat structure of multiple genetic codons used in practicing the present invention, for example, poly(AG) encoding poly(Arg-Glu), poly(AC) encoding poly(Thr-His), poly(AU) encoding poly(Ile-Tyr), and poly(CU) encoding poly(Leu-Ser) are commercially available from SIGMA CHEMICAL COMPANY. Alternatively, mRNAs having a repeat structure of desired genetic codons can be chemically synthesized by a solid phase synthesis based on β-cyanoethyl method, utilizing four RNA nucleotides wherein functional groups are protected (for example, DMT-cyanoethyl RNA phosphoamidite reagents) and a solid phase resin to which a protected RNA nucleotide corresponding to 3'-terminus of RNA to be synthesized is bound, whereby nucleotides are condensed in the order of the desired base sequence (references 19 and 20). Commercially available DNA synthesizer (for example, ABI MODEL 380B; Applied Biosystems) can be used for the synthesis. The synthesized RNA fragment is cut off from the resin, and deprotection of 2'-hydroxyl protecting group is performed (for example, by treating the RNA fragment with a tetrahydrofuran solution containing 1M tetrabutylammonium fluoride at room temperature for 6 hours). The resulting RNA fragment is then purified by high-performance reverse phase chromatography (for example, by using WATERS μ-BONDASPHERE 5μC18–300 column, and eluting the RNA fragment with an acetonitrile linear gradient). The synthetic mRNA is used as a template in the present method.

An aminoacyl-tRNA used in practicing the present invention can be prepared by the method of Nishimura et al.(reference 6) using aminoacyl-tRNA synthetase. Thus, to an amino acid-specific tRNA to be aminoacylated are added a desired amino acid, adenosine triphosphate (ATP) and aminoacyl-tRNA synthetase, and the mixture is reacted in a suitable buffer solution. Proteins are removed from the reaction mixture by phenol extraction and the resulting aminoacyl-tRNA is recovered by ethanol precipitation. Amino acid-specific tRNAs as a substrate and aminoacyl-tRNA synthetase (*E. coli*-derived) are commercially available from SIGMA CHEMICAL COMPANY.

As a synthetic method of a misaminoacyl-tRNA, the method of S. M. Heckler et al. (reference 21) is known. Thus, dinucleotide pCpA is first synthesized chemically and an amino acid is chemically ester-bonded to 3'-terminus of pCpA to obtain aminoacyl-pCpA. On the other hand, tRNA is partially digested with venom phosphodiesterase to obtain tRNA-C-OH lacking pCpA at its 3'-terminus. Finally, the aminoacyl-pCpA is enzymatically linked to the 3'-terminus of tRNA-C-OH using RNA ligase to obtain an aminoacyl-tRNA.

Components and reaction conditions used in a standard system for in vitro protein synthesis (for example, synthesis of polyphenylalanine depending on poly U) are as follows (reference 22). Thus, a reaction mixture (100–500 μl) containing 20–60 mM Tris-HCl (pH 7.0–8.0), 10–15 mM magnesium chloride or magnesium acetate, 10–100 mM $NH_4Cl$, 1–10 mM 2-mercaptoethanol or dithiothreitol, 1–2 mM adenosine triphosphate (ATP), 0.1–0.5 mM guanosine triphosphate (GTP), 5–15 mM sodium phosphoenolpyruvate, 2–50 μg/ml pyruvate kinase, 50–170 μM non-labeled amino acid (excepting phenylalanine), 5–100 μM labeled phenylalanine (for example, 10–100 μCi/μmol of L-[U-$^{14}$C]-phenylalanine), 0.1–1 mg/ml phenylalanine-specific tRNA, 0.1–0.8 mg/ml poly U, 2–50 $A_{260}$ units/ml ribosome, and 2 mg/ml S-100 fraction is incubated at about 37° C. for 15–30 minutes.

Identification of reaction products is generally carried out as follows. Thus, 1 ml of 10% trichloroacetic acid (TCA) solution was added to the mixture and it was heated to 90° C. for 20 minutes to eliminate the amino acid and peptide from the aminoacyl-tRNA and peptidyl-tRNA. Next, the precipitation is collected onto a glass microfiber filter (for example, GF/C, Whatman International Ltd.), and washed four times with 5% TCA and four times with 99% ethanol. After drying, the filter was soaked in 5 ml of liquid scintillation cocktail (for example, ECONOFLUOR-2, NEN Research Products) and the radioactivity of the precipitation on the filter is measured by a liquid scintillation counter (for example, BECKMAN Model LS5000TD) to estimate an amount of the formed product.

For purifying the product from the reaction mixture, various methods used for purifying a protein can be generally utilized. Thus, purification methods such as polyacrylamide gel electrophoresis, isoelectric focusing, ion exchange chromatography, molecular sieve chromatography, and affinity chromatography can be used for purifying the product.

The present invention is further illustrated by the following Examples, but should not be construed to be limited thereto.

EXAMPLE 1

Synthesis of peptides by a step reaction using naturally-occurring aminoacyl-tRNAs and a system for in vitro protein synthesis A tripeptide was synthesized by a step reaction using naturally-occurring aminoacyl-tRNAs in a system for in vitro protein synthesis containing *Escherichia coli* ribosome and S-100 fraction as well as an artificial mRNA.

A. Preparation of *E. coli* ribosome and S-100 fraction as well as properties and activity of purified ribosome A-1. Cultivation of *E. coli*

*E. coli* MRE600 (ATCC No. 29417) was obtained from American Type Culture Collection. L-Broth medium was prepared by dissolving 10 g of Bacto-tryptone (Difco Laboratories), 5 g of Bacto-yeast extract (Difco Laboratories), 5 g of NaCl and 1 g of glucose in 1 L of super purified water and then adjusting at pH 7.5, and was used after autoclaving. Super purified water was prepared by MILLI-Q SP system (Japan Millipore Ltd.). *E. coli* MRE600 cells were cultured overnight in 3 ml of L-broth. The culture was then used to inoculate 1 L of L-broth and cultivation was further continued at 37° C. for 2.0 to 1.5 hours ($A_{600}$=0.4–0.6). The *E. coli* cells were harvested by centrifuging the culture at 10,000×g for 15 minutes and stored at −20° C. until they were used as a starting material for preparing ribosome.

A-2. Preparation of ribosome and S-100 fraction

*E. coil* 70S ribosome and S-100 fraction were prepared by somewhat modifying the method of Noll et al.(reference 18). All procedures were carried out below 4° C. To frozen *E. coli* cells was added two volumes of aluminum oxide, and the mixture was ground in a mortar. When the *E. coli* cells and aluminum oxide were well mixed and the mixture showed a very high viscosity and crackled upon grinding it in the mortar, then equal volume of buffer A (20 mM Tris-HCl, 10 mM $(CH_3COO)_2Mg$, 100 mM $NH_4Cl$, 3 mM 2-mercaptoethanol (pH 7.5)) was added to the mixture, and DNase I (Takara Shuzo K.K.) was further added to obtain 3 μg/ml of final concentration. The suspension was again ground for about 10 minutes. When viscosity of the suspension well lowered, it was centrifuged at 30,000×g for 45 minutes to obtain supernatant (S-30 fraction). The S-30 fraction was overlayered on equal volume of buffer B (10 mM Tris-HCl (pH 7.5) containing 1.1M sucrose, 10 mM $(CH_3COO)_2Mg$, 60 mM $NH_4Cl$, and 3 mM 2-mercaptoethanol), and it was centrifuged using ultracentrifuge for separation BECKMAN MODEL L8M at 100,000×g (Type 45 Ti rotor, 30,000×rpm) for 20 hours. Clear precipitation was recovered as ribosome and upper layer (⅔ of supernatant) as crude S-100 fraction.

The clear precipitation of ribosome was gently suspended in buffer A and the suspension was gently stirred for about 2 hours to disperse ribosome. The resulting ribosome solution was again overlayered on buffer B and it was centrifuged at 100,000×g (Type 45 Ti rotor, 30,000×rpm) for 20 hours. The resulting precipitation of ribosome was again suspended in buffer A and the suspension was then dialyzed against buffer A. The dialyzed suspension was used as ribosome solution in later experiments. Concentration of ribosome was determined by measuring absorbance of the resulting ribosome solution at 260 nm. The solution showing 1.0 of absorbance at 260 nm was defined as 1.0 U/ml ribosome solution. The ribosome solution was stored at −80° C. until use.

The crude S-100 fraction was further fractionated using 70% saturated ammonium sulfate and the precipitated fraction was dialyzed against buffer A. The dialyzed fraction was used as S-100 fraction in later experiments. Protein concentration of the S-100 fraction was determined by measuring absorbance of the resulting fraction at 280 nm. The S-100 fraction was stored at −80° C. until use.

A-3. Properties of purified ribosome

About 8,000 U of ribosome (1U=1$A_{260}$) was obtained from 3 L of *E. coli* cultured medium. For the purpose of assaying the purity of the resulting purified ribosome, it was analyzed by sucrose density-gradient ultracentrifugation in the presence of 10 mM and 1 mM magnesium ion.

The purified ribosome was analyzed by ultrafugation using 10% to 30% of sucrose density-gradient in the presence of 10 mM $Mg^{2+}$ and 1 mM $Mg^{2+}$. The sucrose density-gradient was prepared as follows. Solutions of 3 mM 2-mercaptoethanol, 60 mM $NH_4Cl$, 1 mM or 10 mM $(CH_3COO)_2Mg$, 10 mM Tris-HCl (pH 7.5) each containing 10%, 15%, 20%, 25%, and 30% of sucrose were prepared, and 7.4 ml portions of the solutions were overlayered in order of the sucrose density using a syringe in a centrifugation tube (total volume 37 ml), charging the solution having the lowest sucrose density at the bottom of the tube. The tube was then allowed to stand overnight at 4° C. and sucrose density-gradient was formed. Each of solutions (0.1 ml) of 1 mM or 10 mM $(CH_3COO)_2Mg$, 3 mM 2-mercaptoethanol, 60 mM $NH_4Cl$, 10 mM Tris-HCl (pH 7.5) containing 20 U of ribosome was overlayered onto the sucrose density-gradient solution having the same $Mg^{2+}$ concentration, and the tube was centrifuged at 160,000 ×g (SW28, 20,000 rpm) for 15 hours. After the centrifugation, the sucrose density-gradient solution was taken in 1 ml portions from the bottom of the tube.

Figure 1:
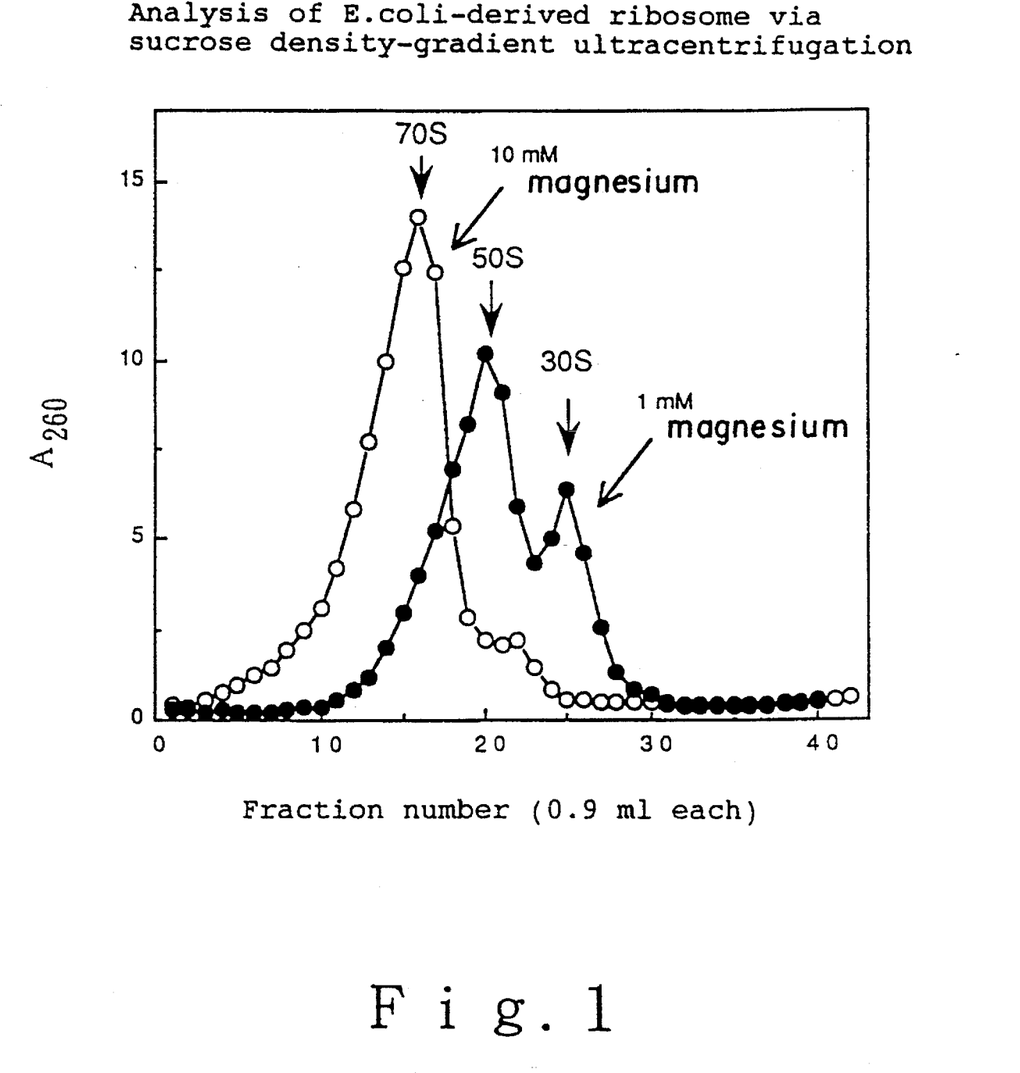
FIG. 1 is a graph depicting the result of sucrose density-gradient ultracentrifugation analysis of *E. coil*-derived ribosome, wherein the line with the open circles represents the result in the presence of 10 mM magnesium while the line with the closed circles represents the result in the presence of 1 mM magnesium.

As a result, in the presence of 10 mM magnesium, only 70S ribosome which is an active form was detected among all ribosomes and 50S and 30S ribosome subunits were little detected (FIG. 1). On the other hand, in the presence of 1 mM magnesium, 70S ribosome was dissociated into 50S and 30S subunits in near completeness.

These results indicated that the ribosome prepared retained a sufficient purity.

A-4. Activity of purified ribosome

For the purpose of examining a protein synthesis activity of the purified ribosome, an activity for polyphenylalanine synthesis was then determined in a system for in vitro protein synthesis using the purified ribosome and polyuridylic acid as a template.

A reaction for in vitro protein synthesis utilizing polyuridylic acid, ribosome and S-100 fraction was carried out by somewhat modifying the method of Spedding et al. (reference 22). Thus, to 10 μl of 10-fold concentrated buffer (0.5M Tris-HCl buffer (pH 8.0) containing 0.1M $MgCl_2$, 0.5M $NH_4Cl$, 10 mM dithiothreitol (DTT), 10 mM adenosine triphosphate (ATP), 10 mM guanosine triphosphate (GTP), and 50 mM sodium phosphoenolpyruvate) were added 1 μl of 3,500 U/ml pyruvate kinase (Oriental Yeast Kogyo K.K.), 10 μl of 20 U/ml phenylalanine-specific tRNA (SIGMA CHEMICAL COMPANY), 1 μl of 140 U/μl ribonuclease inhibitor (Takara Shuzo K.K.), 10 μl of 24 mg/ml S-100 fraction, 10–200 U of purified ribosome, −20 μg of sodium polyuridylate (Yamasa Shoyu K.K.), and 1 μCi of L-[2,3,4,5,6-$^3$H]-phenylalanine (130 Ci/mmol; Amersham Japan K.K.). Then, water was added to make 100 μl of final volume and the mixture was reacted at 37° C. for 15 minutes. After the reaction, 1 ml of 10% trichloroacetic acid (TCA) solution was added to the mixture and it was heated to 90° C. for 20 minutes. The precipitation was collected onto a glass microfiber filter (GF/C, Whatman International Ltd.), and washed four times with 5% TCA and four times with 99% ethanol. After drying, the filter was soaked in 5 ml of liquid scintillation cocktail ECONOFLUOR-2 (NEN Research Products) and the radioactivity of the precipitation on the filter was measured by a liquid scintillation counter (BECKMAN Model LS5000TD).

Figure 2:
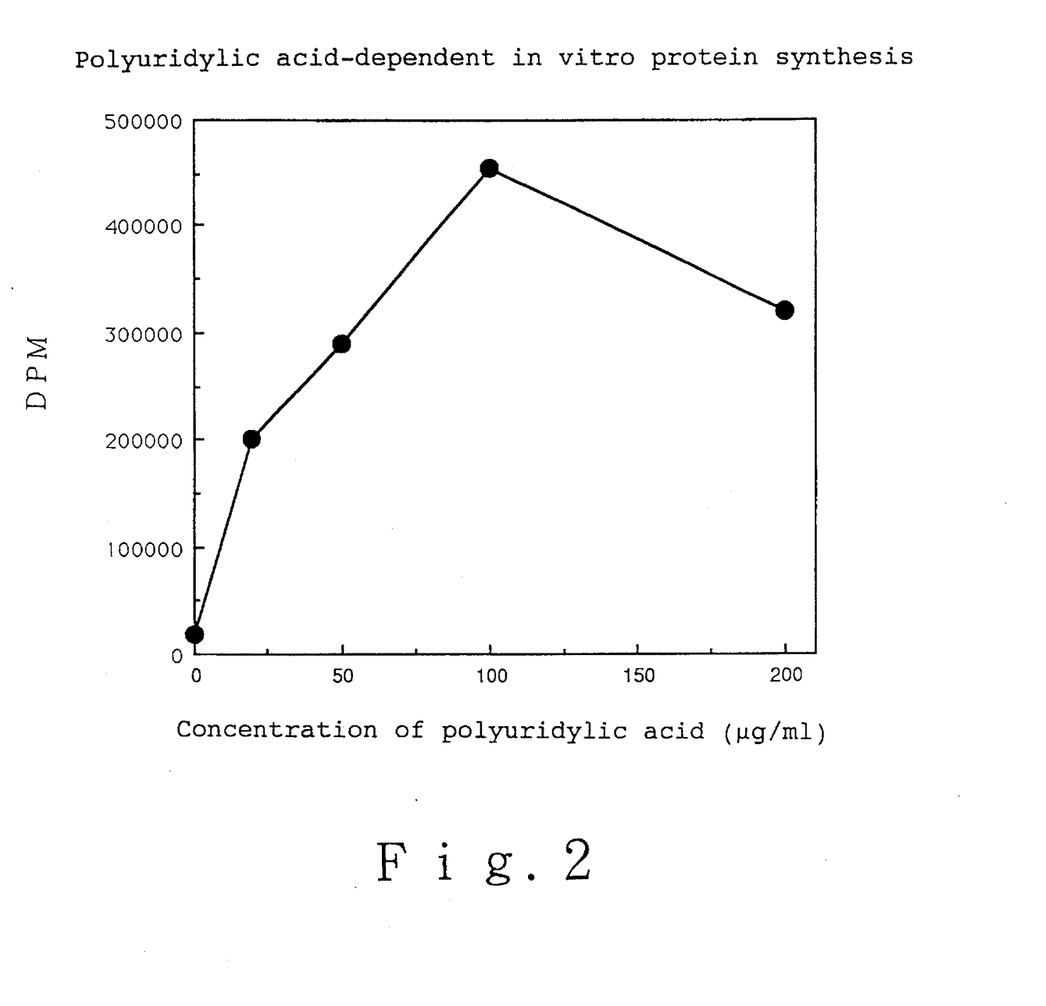
FIG. 2 is a graph depicting the result of in vitro synthesis of a protein by altering concentration of polyuridylic acid.

As a result, it was found that the rate of a radioactive amino acid incorporated into the TCA-insoluble fraction was 0.4 pmol/minute/nmol ribosome and depended on an amount of polyuridylic acid in the reaction solution (FIG. 2).

These results indicated that the ribosome prepared retained a sufficient activity.

B. Chemical synthesis of template mRNA and standard peptide

B-1. Chemical synthesis of template mRNAs

The template mRNAs (AUGUUUGAGUUUGAG: SEQ ID No.1 and UUUGAGUUUGAG: SEQ ID No.2) used in this example were chemically synthesized by DNA synthesizer ABI MODEL 380B (Applied Biosystems), utilizing β-cyanoethyl method using 0.2 μmol of DMT-rG(iBu)-2'-tBuSi-CPG (PENINSULA LABORATORIES, INC.) as a solid phase as well as DMT-rA(Bz)-2'-tBuSi-CEP, DMT-rG(iBu)-2'-tBuSi-CEP, and DMT-U-2'-tBuSi-CEP (PENINSULA LABORATORIES, INC.). After completing the synthesis, the resin was treated with 2 ml of ammonia/ethanol (3/1) solution for 2 hours to cut off a RNA fragment from the resin. The sample was then heated to 55° C. for 8 hours in the ammonia/ethanol (3/1) solution to perform deprotection. The sample was then dried using a centrifugal concentrator under a reduced pressure to dryness. Tetrahydrofuran solution containing 1M tetrabutylammonium fluoride was added to the dry sample at the ratio of 10 μl per 10 $A_{260}$ units of RNA to dissolve the sample. The mixture was maintained at room temperature for hours to perform deprotection of 2'-hydroxyl protecting group. The resulting reaction solution was desalted by gel filtration on NAP-25 column (Pharmacia) eluting with 50 mM triethylamine acetate (TEAA). The resulting RNA fragment was purified by high-performance reverse phase chromatography on WATERS μ-BONDASPHERE 5μC18–300 (3.9 mm×15 cm) column. Thus, not more than 500 μl of the RNA solution was poured on the column, and the desired RNA fragment was eluted with 0% to 20% acetonitrile linear gradient containing 50 mM TEAA. Fractions containing the RNA fragment were pooled and dried using a centrifugal concentrator under a reduced pressure to dryness. The dried sample was then dissolved in water and absorbance at 260 nm was measured.

B-2. Chemical synthesis of standard peptides

Standard tripeptide (Phe-Glu-Phe) and tetrapeptide (Phe-Glu-Phe-Glu: SEQ ID No.3) were chemically synthesized by automated peptide synthesizer ABI MODEL 430A (Applied Biosystems), utilizing t-Boc method using p-methyl BHA resin as a solid phase resin. A synthetic peptide cut off from the resin was purified by a high-performance reverse phase chromatography on WATERS μ-BONDASPHERE 5μC18–300 (3.9 mm×15 cm) column. An amino acid sequence of the purified peptide was analyzed by protein sequencer MODEL 477A (Applied Biosystems).

C. Separation of ribosome-mRNA-peptidyl tRNA complex by high-performance molecular sieve chromatography A process for synthesizing a tripeptide by an in vitro step reaction system utilizing a synthetic mRNA and a naturally-occurring aminoacyl-tRNA was constructed by Initiation reaction cycle, Peptide extension reaction cycle, and Termination reaction cycle.

Firstly, the Initiation reaction cycle was defined as a process composed of the following three steps: (a-1) reaction of an aminoacyl-tRNA or misaminoacyl-tRNA (wherein a N-terminal amino acid of a desired peptide binds to tRNA) with ribosome and mRNA to form a ribosome-mRNA-(mis)aminoacyl tRNA complex; (a-2) separation of the ribosome-mRNA-(mis)aminoacyl tRNA complex by high-performance molecular sieve chromatography; and (a-3) concentration of fractions containing the complex by ultrafiltration.

Next, the Peptide extension reaction cycle was defined as a process composed of the following three steps: (b-1) peptide formation reaction comprising binding a next amino acid residue on the previous ribosome-mRNA-peptidyl tRNA complex; (b-2) separation of the resulting ribosome-mRNA-peptidyl tRNA complex by high-performance molecular sieve chromatography; and (b-3) concentration of fractions containing the complex by ultrafiltration.

Finally, the Termination reaction cycle was defined as a process composed of the following three steps: (c-1) recovery of the peptidyl-tRNA from the final ribosome-mRNA-peptidyl tRNA complex by phenol extraction and ethanol precipitation; (c-2) elimination of the desired peptide from the peptidyl-tRNA by hydrolysis of RNA; and (c-3) purification of the desired peptide by high-performance reverse phase chromatography.

Synthesis of a tripeptide by a step reaction was accomplished by carrying out the Initiation reaction cycle, then repeating twice the Peptide extension reaction cycle, and finally performing the Termination reaction cycle.

However, for the realization of the above-constructed step reaction system by a system for in vitro protein synthesis, the ribosome-mRNA-aminoacyl tRNA complex and the ribosome-mRNA-peptidyl tRNA complex must be separated from tRNA and other amino acid components by a molecular sieve chromatography, and furthermore, they must be stably retained during the course of separation and/or concentration.

Accordingly, a complex was prepared using the above-prepared ribosome, synthetic mRNA and an aminoacyl-tRNA, separated by the following molecular sieve chromatography, and further analyzed by sucrose density-gradient ultracentrifugation (carrying out in a similar manner as described in the above A-3).

Molecular sieve chromatography

The ribosome-mRNA-peptidyl tRNA complex was separated by high-performance molecular sieve chromatography on Shodex PROTEIN KW-803 columns (8 mm×30 cm, paired). Waters 600E Multisolvent Delivery System was used as a solvent delivery system. The columns were previously equilibrated using 10 mM Tris-Cl buffer (pH 7.5) containing 60 mM $NH_4Cl$ and 10 mM $(CH_3COO)_2Mg$. Not more than 200 μl of the sample solution containing the ribosome-mRNA-peptidyl tRNA complex was applied to the columns and developed at a rate of 1.0 ml/min. Absorbance at 260 nm of the eluted solution was monitored by Waters 484 Tunable Absorbance Detector, and the results were recorded by Waters 741 Data Module. Fractions were collected in 0.5 ml portions. To 0.5 ml of each fraction was added 2 ml of liquid scintillation cocktail Ready Safe (BECKMAN Instrument, Inc.) and the radioactivity of the mixture was measured by a liquid scintillation counter (BECKMAN Model LS5000TD). Protein markers for molecular weight determination on HPLC were purchased from Oriental Yeast Kogyo K.K. The markers used were glutamic dehydrogenase (Mw 290,000), lactate dehydrogenase (Mw 142,000), enolase (Mw 67,000), adenylate kinase (Mw 32,000), and cytochrome C (Mw 12,400).

Figure 3:
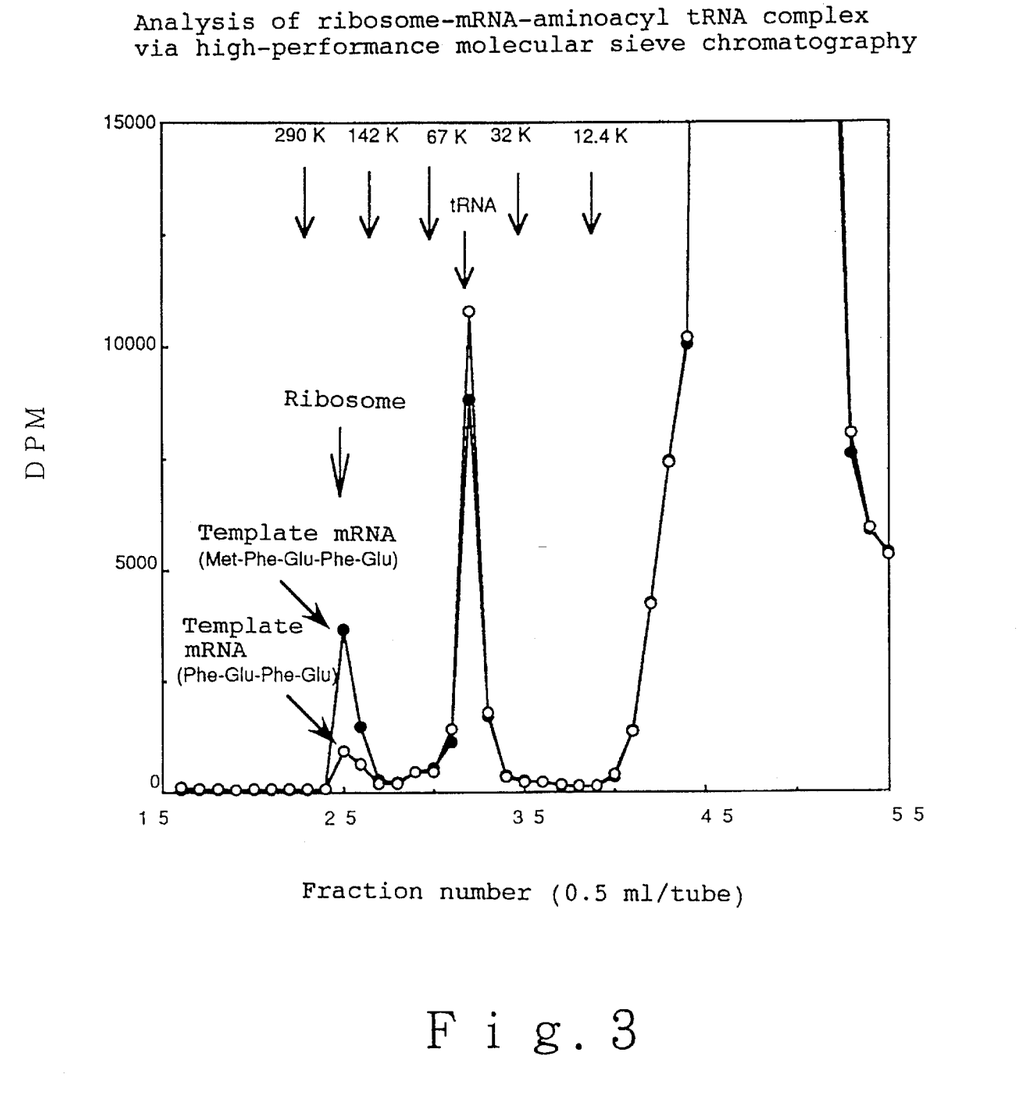
FIG. 3 is a graph depicting the result of high-performance molecular sieve chromatography analysis of a ribosome-mRNA-aminoacyl tRNA complex.
Figure 4:
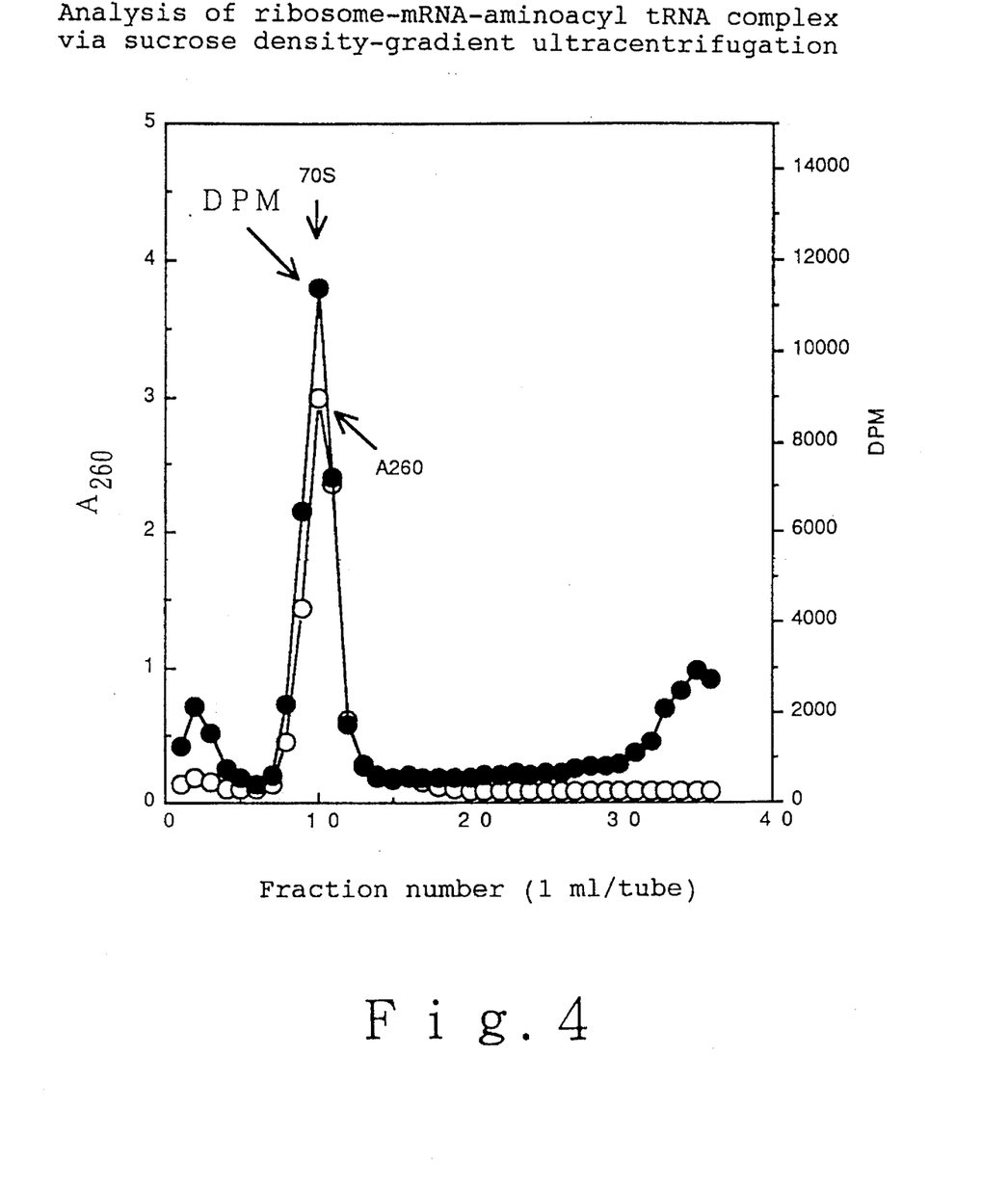
FIG. 4 is a graph depicting the result of sucrose density-gradient ultracentrifugation analysis of a ribosome-mRNA-aminoacyl tRNA complex.

When radioactive methionine was allowed to incorporate into ribosome in a system for in vitro protein synthesis utilizing the template mRNA (AUGUUUGAGUUUGAG: SEQ ID No.1) encoding the amino acid sequence of Met-Phe-Glu-Phe-Glu (SEQ ID No.4) and the reaction mixture was subsequently fractionated by high-performance molecular sieve chromatography on Shodex KW-803 column, then ribosome was eluted in the void fraction, tRNA eluted in fractions corresponding to a molecular weight of about 60,000, and the free radioactive amino acid eluted in fractions corresponding to a low molecular weight of not more than 10,000, respectively. Incorporation of the radioactive amino acid was observed both in the void fraction and in the tRNA fractions (FIG. 3). When the void fraction containing the radioactivity was analyzed by sucrose density-gradient ultracentrifugation, it was found that most of the radioactivity was recovered in fractions containing 70S ribosome and the radioactive amino acid bound to 70S ribosome (FIG. 4).

On the other hand, when radioactive methionine was similarly allowed to incorporate into ribosome in a system for in vitro protein synthesis utilizing the template mRNA (UUUGAGUUUGAG: SEQ ID No.2) encoding the amino acid sequence of Phe-Glu-Phe-Glu (SEQ ID No.3) and the reaction mixture was subsequently fractionated by high-performance molecular sieve chromatography, then similar incorporation of the radioactive amino acid into the tRNA fractions was observed as in the case of using AUGUUUGAGUUUGAG (SEQ ID No.1) as a template but incorporation of the radioactive amino acid into the ribosome fractions was little observed.

Accordingly, it is possible to conclude that the radioactive amino acid bound to ribosome only when AUG codon existed in the template mRNA.

Figure 5:
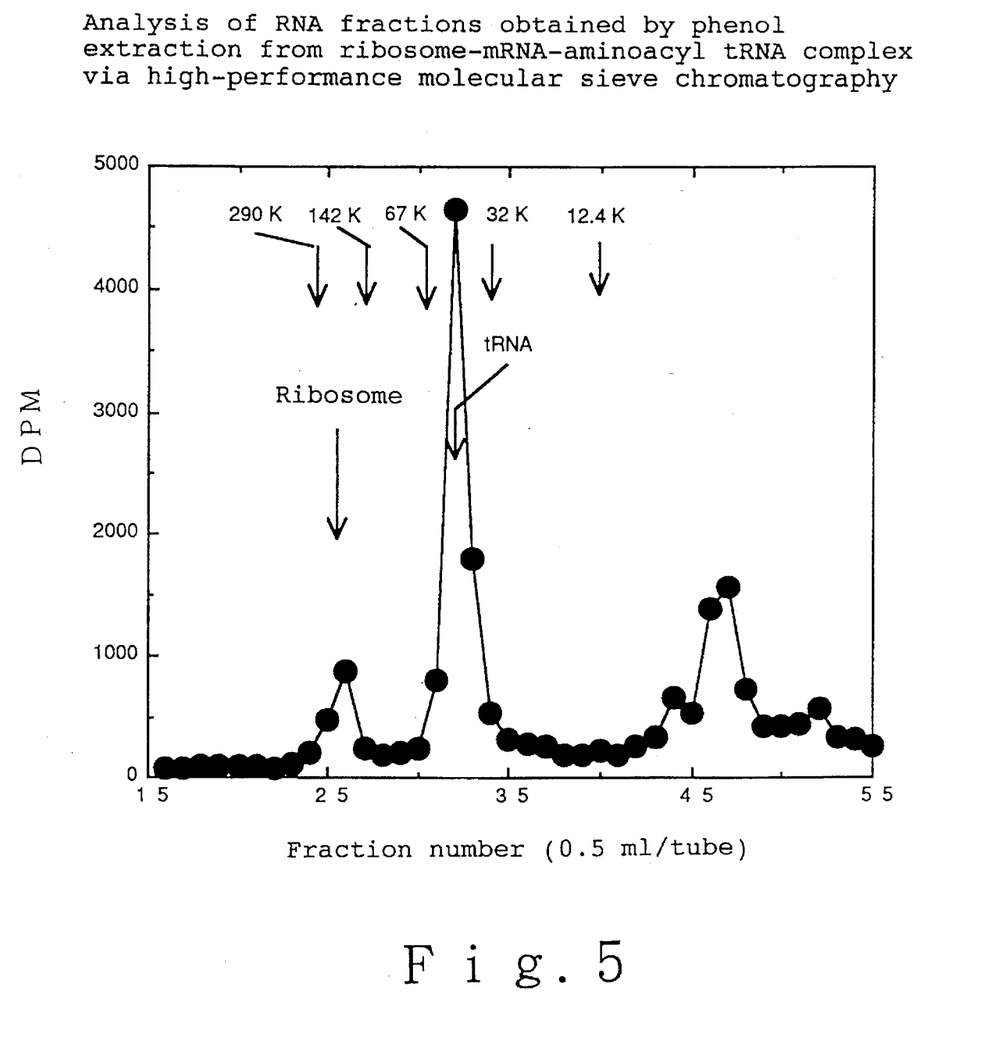
FIG. 5 is a graph depicting the result of high-performance molecular sieve chromatography analysis of an RNA fraction obtained by phenol extraction from a ribosome-mRNA-aminoacyl tRNA complex.

Next, when the ribosome fractions containing the radioactivity were treated with phenol and the RNA fractions were recovered and again analyzed by high-performance molecular sieve chromatography, then it was found that most of the radioactivity was eluted in tRNA fractions and the aminoacyl-tRNA bound to ribosome (FIG. 5). In addition, when the ribosome fractions containing the radioactivity were again analyzed by high-performance molecular sieve chromatography, most of the radioactivity was recovered in 70S ribosome fractions (data not shown).

The above results indicate that the ribosome-mRNA-aminoacyl tRNA complex formed by in vitro protein synthesis was separated from tRNA and other components by high-performance molecular sieve chromatography, and that the complex stably existed even in the course of high-performance molecular sieve chromatography and sucrose density-gradient ultracentrifugation.

D. Synthesis of peptide in system for in vitro protein synthesis

A peptide was synthesized in a system for in vitro protein synthesis utilizing as a template an artificial mRNA encoding the amino acid sequence of Met-Phe-Glu-Phe-Glu (SEQ ID No.3).

D-1. Synthesis of peptide in serial reaction system

Figure 6:
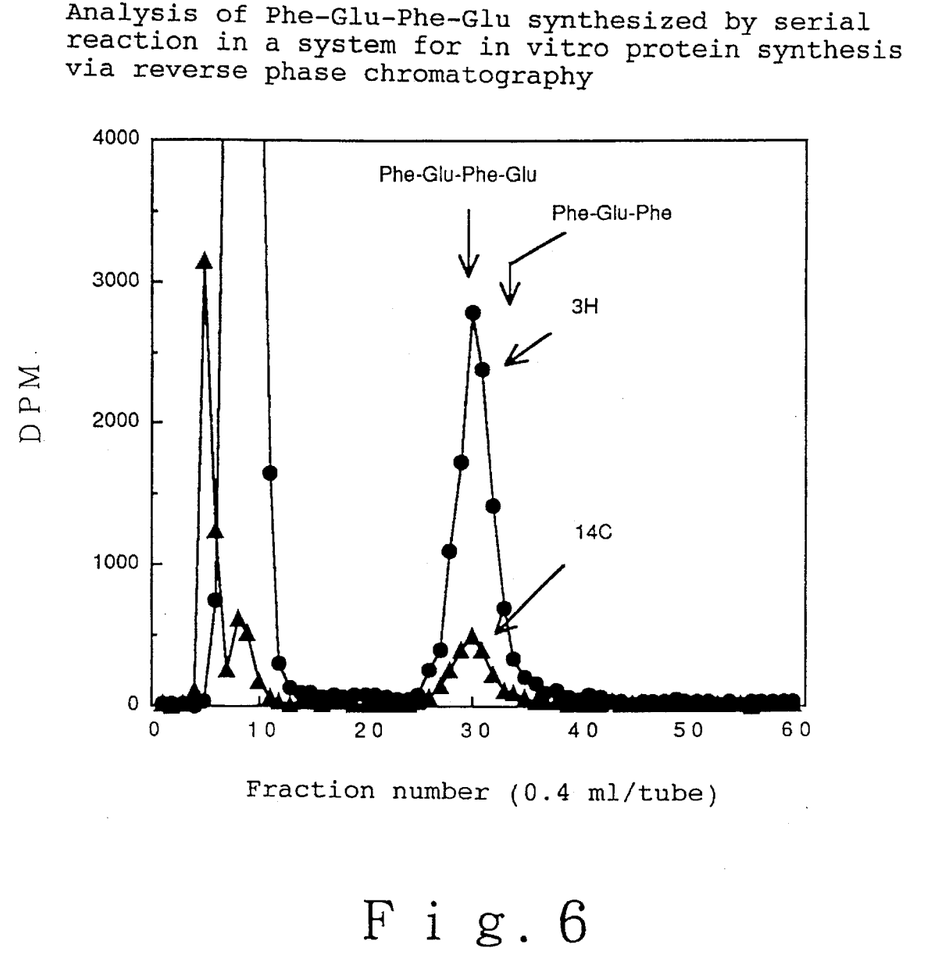
FIG. 6 is a graph depicting the result of reverse phase chromatography analysis of Phe-Glu-Phe-Glu synthesized by serial reaction in a system for in vitro protein synthesis.

As a control, $^3$H-Phe and $^{14}$C-Glu were first added to a reaction system for in vitro protein synthesis to serially synthesize a peptide for 15 minutes. Ribosome was then recovered by high-performance molecular sieve chromatography and the formed peptide was eliminated from the peptidyl-tRNA bound to ribosome by phenol treatment and alkaline hydrolysis. The recovered product was analyzed by high-performance reverse phase chromatography. As a result, peaks regarded as those of free $^3$H-Phe and $^{14}$C-Glu were detected at elution positions of $^3$H-Phe and $^{14}$C-Glu, and both radioactivities of $^3$H-Phe and $^{14}$C-Glu were detected at an elution position of standard Phe-Glu-Phe-Glu (SEQ ID No.3) chemically synthesized (FIG. 6).

These results indicate that when peptide synthesis was carried out in a system for in vitro protein synthesis utilizing as a template an artificial mRNA encoding the amino acid sequence of Met-Phe-Glu-Phe-Glu (SEQ ID No.4), then the amino acids added were incorporated into aminoacyl-tRNAs, which in turn formed a complex together with ribosome and mRNA. The results also indicate that part of peptidyl of the complex further grew to a peptide chain by extension reaction and consequently tetrapeptide Phe-Glu-Phe-Glu (SEQ. ID No. 3) encoded by the mRNA was synthesized.

D-2. Synthesis of peptide in step reaction system

Next, a stepwise synthesis of Phe-Glu-Phe was attempted by using a step reaction system using the same mRNA as a template and carrying out two extension reaction cycles.

Initiation reaction cycle (Cycle-0):

To 20 μl of 10-fold concentrated buffer for protein synthesis were added 2 μl of 3,500 U/ml pyruvate kinase, 20 μl of 20 U/ml phenylalanine-specific tRNA (SIGMA CHEMICAL COMPANY), 2 μl of 140 U/μl ribonuclease inhibitor, 20 μl of 24 mg/ml S-100 fraction, 10–200 U of purified ribosome, 40 μl of 40 μM synthetic mRNA, and 20 μl of 1 mM phenylalanine. Water was then added to make 200 μl of final volume and the mixture was reacted at 37° C. for 15 10 minutes. After the reaction, the reaction mixture was fractionated by high-performance molecular sieve chromatography on Shodex PROTEIN KW-803 columns (8 mm×30 cm, paired) and fractions containing ribosome were pooled. The ribosome fractions were then combined and concentrated to about 50 μl of volume by centrifugal ultrafiltration using Centricon-30 (## Grease Japan K.K.). The resulting concentrated solution was used as a ribosome-mRNA-phenylalanyl tRNA$^{Phe}$ complex fraction.

Peptide extension reaction cycle (Cycle-1):

To the ribosome-mRNA-phenylalanyl tRNA$^{Phe}$ complex fraction obtained in Cycle-0 were added 20 μl of 10-fold concentrated buffer for protein synthesis, 2 μl of 3,500 U/ml pyruvate kinase, 20 μl of 20 U/ml glutamic acid-specific tRNA (SIGMA CHEMICAL COMPANY), 2 μof 140 U/μl ribonuclease inhibitor, 20 μl of 24 mg/ml S-100 fraction, and 1 μCi of L-[U-$^{14}$C]-glutamic acid (270 mCi/mmol; Amersham Japan K.K.). Water was then added to make 200 μl of final volume and the mixture was reacted at 37° C. for 15 minutes. After the reaction, the reaction mixture was fractionated by high-performance molecular sieve chromatography as described in Cycle-0 and fractions containing ribosome were collected. The ribosome fractions were then combined and concentrated to about 50 μl of volume by Centricon-30. The resulting concentrated solution was used as a ribosome-mRNA-phenylalanyl glutamic acidyl tRNA$^{Glu}$ complex fraction.

Peptide extension reaction cycle (Cycle-2):

To the ribosome-mRNA-phenylalanyl glutamic acidyl tRNA$^{Glu}$ complex fraction obtained in Cycle-1 were added 20 μl of 10-fold concentrated buffer for protein synthesis, 2 μl of 3,500 U/ml pyruvate kinase, 20 μof 20 U/ml phenylalanine-specific tRNA (SIGMA CHEMICAL COMPANY), 2 μl of 140 U/i ribonuclease inhibitor, 20 μl of 24 mg/ml S-100 fraction, and 1 μl Ci of L-[2,3,4,5,6-$^3$H]-phenylalanine (130 Ci/mmol; Amersham Japan K.K.). Water was then added to make 200 μl of final volume and the mixture was reacted at 37° C. for 15 minutes. After the reaction, the reaction mixture was fractionated by high-performance molecular sieve chromatography. The resulting ribosome fractions were then combined and used as a ribosome-mRNA-phenylalanyl glutamic acidyl phenylalanyl tRNA$^{Phe}$ complex fraction.

Termination reaction cycle (Cycle-END):

To the ribosome-mRNA-phenylalanyl glutamic acidyl phenylalanyl tRNA$^{Phe}$ complex fraction obtained in Cycle-2 was added equal volume of TE-saturated phenol solution. The resulting suspension was centrifuged at 10,000×g for 10 minutes. The resulting water phase was extracted with chloroform/isoamylalcohol (24:1). To the water phase was added two volumes of 99% ethanol and the mixture was allowed to stand for 20 minutes at −80° C. The mixture was then centrifuged at 10,000×g for 10 minutes to precipitate RNA. The resulting RNA precipitation was dissolved in 100 μl of 0.1N KOH and RNA was hydrolyzed at 37° C. for 30 minutes. After the reaction, 100 μl of 0.1N HCl was added to the reaction mixture to neutralize it. The neutralized reaction mixture was poured onto μ-BONDASPHERE 5μC18–300 (3.9 mm×15 cm) column, and the desired phenylalanyl-glutamic acidyl-phenylalanine was eluted with 12% to 51% acetonitrile linear gradient containing 0.1% trifluoroacetic acid (TFA). Fractions were collected in 0.5 ml portions. To 0.5 ml of each fraction was added 2 ml of liquid scintillation cocktail Ready Safe (BECKMAN Instrument, Inc.) and the radioactivity of the mixture was measured by a liquid scintillation counter (BEC/AN Model LS5000TD).

Figure 7:
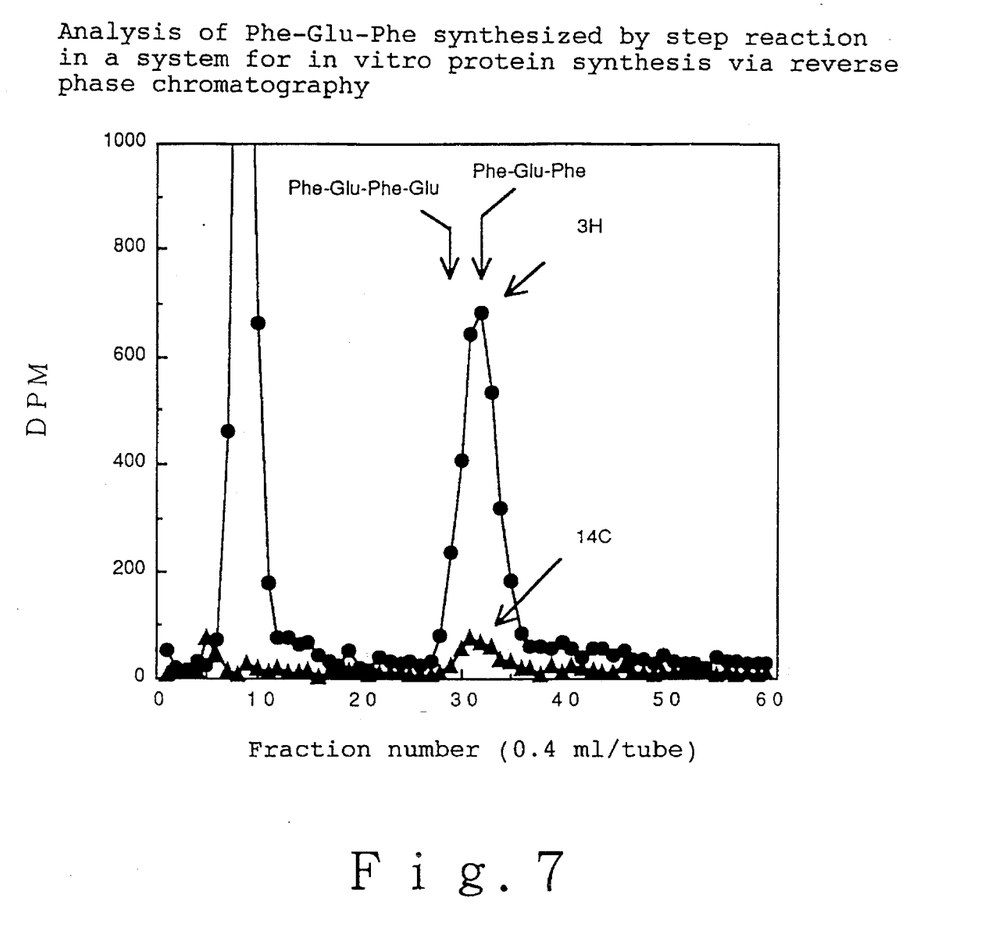
FIG. 7 is a graph depicting the result of reverse phase chromatography analysis of Phe-Glu-Phe synthesized by step reaction in a system for in vitro protein synthesis.

The product recovered in the above termination reaction cycle was analyzed by high-performance reverse phase chromatography. As is similar to the case in the serial reaction system, peaks regarded as those of free $^3$H-Phe and $^{14}$C-Glu were detected at elution positions of $^3$H-Phe and $^{14}$C-Glu, and both radioactivities of $^3$H-Phe and $^{14}$C-Glu were detected at an elution position of standard Phe-Glu-Phe chemically synthesized (FIG. 7).

These results indicate that in the stepwise reaction system, similar to the case in the serial reaction system, the amino acid added in the initiation reaction was incorporated into aminoacyl-tRNAs, which in turn formed a complex together with ribosome and mRNA. The results also indicate that part of peptidyl of the complex further grew to a peptide chain in the extension reactions and consequently tripeptide Phe-Glu-Phe encoded by the mRNA was synthesized.

As described above, the results obtained in this example indicate that a peptide having a desired amino acid sequence can be synthesized by a step reaction system for in vitro protein synthesis utilizing ribosome, an aminoacyl-tRNA or misaminoacyl-tRNA, and an artificial mRNA having a predetermined sequence.

References

1. F. C. McKay and W. F. Albertson, J. Am. Chem. Soc., 79, 4686 (1957).
2. L. A. Carpino and G. Y. Han, J. Am. Chem. Soc., 92, 5748 (1970).
4. R. B. Merrifield, J. Am. Chem. Soc., 85, 2149 (1963).
5. M. Bergmann and H. Fraenkel-Conrat, J. Biol. Chem., 124,1 (1938).
6. T. Oka and K. Morihara, J. Biochem.(Tokyo), 84, 1277 (1978).
7. H. Takai, K. Sakato, N. Nakamizo and Y. Isowa, "Peptide Chemistry 1980", K. Okawa ed., Protein Research Foundation, p.213 (1981).
8. H. Nakajima, S. Kitabatake, R. Tsurutani, I. Tomioka, K. Yamamoto and K. Imahori, BIochim. Biophys. Acta, 790, 197 (1984).
10. M. W. Nirenberg and J. H. Matthaei, Proc. Natl. Acad. Sci. USA, 47, 1588 (1961).
11. A. S. Spirin, V. I. Baranov, L. A. Ryabova, S. U. Ovodov and Y. B. Alahhov, Science, 242, 1162 (1988).
12. T. G. Heckler, L. H. Chang, Y. Zama, T. Naka and S. M. Hecht, Tetrahedron, 40, 87 (1984).
13. T. G. Heckler, L. H. Chang, Y. Zama, T. Naka, M. S. Chorghade and S. M. Hecht, Biochemistry, 23, 1468 (1984).
14. T. G. Heckler, Y. Zama, T. Naka, and S. M. Hecht, J. Biol. Chem., 258, 4492 (1983).
15. J. R. Roesser, M. S. Chorghade and S. M. Hecht, Biochemistry, 25, 6361 (1986).
16. R. C. Payne, B. P. Nichols and S. M. Hecht, Biochemistry, 26, 3197 (1987).
17. C. J. Noren, S. J. Anthony-Cahill, M. C. Griffith and P. G. Schultz, Science, 244 182 (1989).
18. M. Noll, B. Hapke, M. H. Schreier and H. Noll, JH. Mol. Biol., 75, 281 (1973).
19. N. Usman, K. K. Ogilvie, M.-Y. Jiang and R. J. Cedergren, J. Amer. Chem. Soc., 109, 7845 (1987).
20. K. K. Ogilvie, N. Usman, M.-Y. Jiang and R. J. Cedergren, Proc. Natl. Acad. Sci., 16, 5764 (1988).
21. T. G. Heckler, L. H. Chang, Y. Zama, T. Naka, M. S. Chorghade and S.M. Hecht, Biochemistry, 23, 1468 (1984).
22. G. Spedding, "Ribosomes and Protein Synthesis", G. Spedding ed., Oxford University Press, p.25 (1989).

---

What is claimed is:

1. A method for synthesizing a peptide or protein having a desired amino acid sequence by a stepwise extension reaction comprising:

(i) preparing as a template an artificial mRNA having a repeat structure of multiple genetic codons different from each other;

(ii) preparing aminoacyl-tRNAs wherein a corresponding naturally-occurring amino acid binds to tRNA and misaminoacyl-tRNAs wherein a non-corresponding naturally-occurring or non-naturally-occurring amino acid binds to tRNA, in which said aminoacyl-tRNAs and misaminoacyl-tRNAs correspond to each of said multiple genetic codons and are Used in the following step (iii); and (iii) adding one or more aminoacyl-tRNAs or misaminoacyl-tRNAs, wherein an amino acid component to be incorporated into said peptide or protein binds to tRNA, to a system for in vitro protein synthesis containing said mRNA and ribosome, and extending stepwise the chain of said peptide or protein.

2. The method according to claim 1 wherein said stepwise extension reaction is composed of the following three reaction cycles: (a) Initiation reaction cycle wherein an aminoacyl-tRNA or misaminoacyl-tRNA, wherein the N-terminal amino acid of the desired peptide or protein is bound to tRNA, forms a complex together with ribosome and mRNA; (b) Peptide extension reaction cycle wherein a peptide chain is extended stepwise from the second amino acid residue of the desired peptide or protein on the ribosome-mRNA-aminoacyl or misaminoacyl tRNA complex; and (c) Termination reaction cycle wherein the desired peptide or protein is separated from the ribosome-mRNA-peptidyl tRNA complex.

3. The method according to claim 2 wherein Initiation reaction cycle (a) is composed of the following three steps: (a-1) reaction of an aminoacyl-tRNA or misaminoacyl-tRNA, wherein the N-terminal amino acid of the desired peptide or protein is bound to tRNA, with ribosome and mRNA to form a ribosome-mRNA-aminoacyl or misaminoacyl tRNA complex; (a-2) separation of the ribosome-mRNA-aminoacyl or misaminoacyl tRNA complex by high-performance molecular sieve chromatography; and (a-3) concentration of fractions containing the complex by ultrafiltration.

4. The method according to claim 2 wherein Peptide extension reaction cycle (b) is composed of the following three steps: (b-1) peptide formation reaction comprising binding M amino acid residues from the (N+1)th amino acid residue on the ribosome-mRNA-peptidyl tRNA complex, wherein M is an integer of 1 to 63 and N is an integer of 1 or more; (b-2) separation of the resulting ribosome-mRNA-peptidyl tRNA complex by high-performance molecular sieve chromatography; and (b-3) concentration of fractions containing the complex by ultrafiltration.

5. The method according to claim 2 wherein Termination reaction cycle (c) is composed of the following three steps: (c-1) recovery of the peptidyl-tRNA from the final ribosome-mRNA-peptidyl tRNA complex by phenol extraction and ethanol precipitation; (c-2) elimination of the desired peptide or protein from the peptidyl-tRNA by hydrolysis of RNA; and (c-3) purification of the desired peptide or protein by high-performance reverse phase chromatography.

6. The method according to claim 1 wherein the artificial mRNA comprises the following sequence:

$$(A_1 A_2 A_3 \ldots A_m)_n$$

wherein m is an integer of 2 to 64, n is an integer of 1 or more, m×n is equal to the number of amino acid residues of the desired peptide or protein or more, and each of $A_1$, $A_2$, $A_3$, ... and $A_m$ represents a genetic codon which differs from the other codons.

7. The method according to claim 1 wherein misaminoacyl-tRNAs are used.

* * * * *